(12) United States Patent
Constantz

(10) Patent No.: US 6,387,071 B1
(45) Date of Patent: May 14, 2002

(54) METHODS AND DEVICES FOR REDUCING THE MINERAL CONTENT OF VASCULAR CALCIFIED LESIONS

(75) Inventor: Brent R. Constantz, Portola Valley, CA (US)

(73) Assignee: Corazon Technologies, Inc., Menlo Park, CA (US)

( * ) Notice: Subject to any disclaimer, the term of this patent is extended or adjusted under 35 U.S.C. 154(b) by 0 days.

(21) Appl. No.: 09/195,291

(22) Filed: Nov. 18, 1998

Related U.S. Application Data (63) Continuation-in-part of application No. 09/118,193, filed on Jul. 15, 1998.

(51) Int. Cl.[7] .............................................. A61M 3/00
(52) U.S. Cl. ...................... 604/43; 128/898; 604/508
(58) Field of Search .......................... 128/898; 604/27, 604/28, 96.01, 101.01, 43

(56) References Cited

U.S. PATENT DOCUMENTS

| | | | |
|---|---|---|---|
| 3,651,868 A | 3/1972 | Caudle et al. | 166/307 |
| 3,855,914 A | 12/1974 | Nishino et al. | 99/275 |
| 3,860,289 A | 1/1975 | Learmont | 299/4 |
| 4,022,119 A | 5/1977 | Karr | 99/275 |
| 4,049,519 A | 9/1977 | Sloan | 204/180 |
| 4,105,253 A | 8/1978 | Showalter | 299/4 |
| 4,108,764 A | 8/1978 | Kaneko et al. | 210/22 A |
| 4,250,965 A | 2/1981 | Wiseman, Jr. | 166/305 R |
| 4,358,158 A | 11/1982 | Showalter | 299/4 |
| 4,445,892 A | 5/1984 | Hussein et al. | 604/101 |
| 4,573,966 A | 3/1986 | Weikl et al. | 604/53 |
| 4,610,662 A | 9/1986 | Weikl et al. | 604/53 |
| 4,636,195 A | 1/1987 | Wolinsky | 604/53 |
| 4,655,746 A | 4/1987 | Daniels et al. | 604/53 |
| 4,778,006 A | 10/1988 | Derowitsch | 166/267 |
| 4,824,436 A | 4/1989 | Wolinsky | 604/53 |
| 4,911,163 A | 3/1990 | Fina | 606/127 |
| 4,976,733 A | 12/1990 | Giradot | 623/11 |
| 5,059,178 A | 10/1991 | Ya | 604/101 |
| 5,069,664 A | 12/1991 | Guess et al. | 604/22 |
| 5,090,960 A | 2/1992 | Michael | 604/101 |
| 5,140,822 A | 8/1992 | Gupta | 62/50.1 |
| 5,167,628 A | 12/1992 | Boyles | 604/101 |
| 5,171,694 A | 12/1992 | Connolly | 436/134 |
| 5,195,955 A | 3/1993 | Michael | 604/22 |
| 5,222,941 A | 6/1993 | Michael | 604/101 |
| 5,238,845 A | 8/1993 | Tancredi et al. | 436/8 |
| 5,380,284 A | 1/1995 | Michael | 601/101 |
| 5,443,446 A | 8/1995 | Shturman | 604/49 |
| 5,462,529 A | 10/1995 | Simpson et al. | |
| 5,681,507 A | 10/1997 | Kazuma | 261/27 |
| 5,736,072 A | 4/1998 | Satoh | 261/27 |
| 5,758,789 A | 6/1998 | Shin et al. | 215/382 |

FOREIGN PATENT DOCUMENTS

| | | |
|---|---|---|
| WO | 97/40756 | 11/1997 |
| WO | 98/25855 | 6/1998 |

*Primary Examiner*—Corrine McDermott
*Assistant Examiner*—Thom Barrett
(74) *Attorney, Agent, or Firm*—Bret E. Field; Bozicevic, Field & Francis (57) ABSTRACT

Methods and devices are provided for at least reducing the mineral content of a vascular calcified lesion, i.e. a calcified lesion present on the vascular tissue of a host. In the subject methods, the local environment of the lesion is maintained at a subphysiologic pH for a period of time sufficient for the mineral content of the lesion to be reduced, e.g. by flushing the lesion with a fluid capable of locally increasing the proton concentration in the region of the lesion. Also provided are catheters for use in performing the subject methods, where the catheters at least include a first lumen capable of delivering fluid to a vascular site and a second lumen capable of removing fluid from a vascular site. The subject methods and devices find particular use in the treatment of vascular diseases associated with the presence of calcified lesions on vascular tissue.

6 Claims, 4 Drawing Sheets

METHODS AND DEVICES FOR REDUCING THE MINERAL CONTENT OF VASCULAR CALCIFIED LESIONS

CROSS-REFERENCE TO RELATED APPLICATIONS

This application is a continuation-in-part of application Ser. No. 09/118,193 filed on Jul. 15, 1998, the disclosure of which is herein incorporated by reference.

INTRODUCTION

Technical Field

The field of this invention is vascular disease, particularly vascular diseases characterized by the presence of calcified lesions, e.g. atherosclerosis.

BACKGROUND OF THE INVENTION

The formation of plaques or lesions, (atherosclerotic plaques or lesions) on cardiovascular tissue, such as the inner surface of blood vessels, arotic valves, etc., is a major component of cardiovascular disease. Many atherosclerotic plaques and lesions are characterized by the presence of mineral desposits, i.e. they are calcified. Atherosclerotic calcification is thought to be an organized, regulated process similar to bone formation that occurs only when other aspects of atherosclerosis are also present. Calcium phosphate, in the crystalline form of carbonated apatite (dahllite), which contains 40% calcium by weight, precipitates in diseased coronary arteries by mechanisms that appear similar to that found in active bone formation and remodeling (Bostom, K., et al., *J. Clin. Invest.* 91:1800–9, 1993; Lowenstam, H. A., and Wiener, S., *On Biomineralization*, Oxford University Press, N.Y.). Atherosclerotic calcification begins as early as the second decade of life, just after fatty streak formation (Stary, H. C.,*Eur. Heart J.* 11(Suppl. E):3–19, 1990). The lesions of younger adults have revealed small aggregates of crystalline calcium phosphate among the lipid particles of lipid cores (Stary, H. C., et al., *Circulation* 92:1355–74, 1995). Calcific deposits are found more frequently and in greater amounts in elderly individuals and more advanced lesions (Doherty, T. M., and Detrano, R. C., *Calcif. Tissue Int.* 54:224–30, 1994). In most advanced lesions, when mineralization dominates the picture, components such as lipid deposits and increased fibrous tissue may also be present.

Calcified lesion formation on prosthetic devices is also a problem in current cardiovascular disease treatment protocols. For example, calcification is an important limitation on the useful life expectancy of bioprosthetic valves, and accounts for over sixty percent of the cardiac bioprostheses failures.

A variety of different protocols have been developed for treating cardiovascular diseases associated with the presence of calcified lesions. Such treatment methodologies generally involve mechanical removal or reduction of the lesion and include: bypass surgery, balloon angioplasty, mechanical debridement, valve replacement, and the like. Despite the plethora of different treatment strategies that have been developed for the treatment of cardiovascular disease, there are disadvantages associated with each technique, such as tissue damage, invasiveness, etc. For example, restenosis is a common complication that results in arteries in which lesions have been mechanically removed.

As such, there is continued interest in the development of new treatment protocols for the removal of vascular calcified lesions from vascular tissue. Of particular interest would be the development of a treatment protocol that is minimally invasive and results in minimal tissue damage.

Relevant Literature

U.S. Patents of interest include: U.S. Pat. Nos. 4,636,195; 4,976,733; 5,222,941; 5,380,284; and 5,443,446. Other U.S. Patents of interest include: U.S. Pat. Nos. 4,445,892; 4,573, 966; 4,610,662; 4,655,746; 4,824,436; 4,911,163; 5,059, 178; 5,090,960; 5,167,628; and 5,195,955.

SUMMARY OF THE INVENTION

Methods and devices for at least reducing the mineral content of a calcified lesion on vascular tissue are provided. In the subject methods, the local environment of the target lesion is maintained at a subphysiologic pH for a period of time sufficient for the desired amount of demineralization to occur, e.g. by flushing the lesion with a fluid capable of locally increasing the proton concentration in the region of the calcified lesion. As a result, the mineral content of the calcified lesion is reduced. Also provided are catheters for use in the subject methods, where the subject catheters at least include a first lumen for introducing fluid to a vascular site and a second lumen for removing liquid from a vascular site, where the second lumen preferably has a cross-sectional dimension that is sufficiently large to allow passage of lesion debris. The subject methods and devices find use in the treatment of vascular diseases associated with the presence of calcified lesions.

DEFINITIONS

The term "vascular tissue" is used herein in its broadest sense to refer to any tissue which is part of the circulatory system of a host. As such, the term vascular tissue includes arteries and veins, as well as specialized organs that are closely associated with the vascular system, such as the heart, kidney, and the like, as well as specialized features of vessels or organs, such as valves, chambers, etc. The term "vascular tissue" further includes prosthetic devices that are implanted into the circulatory system of a host, e.g. prosthetic valves, etc.

The term "cardiovascular tissue" as used herein refers to any kind of vascular tissue which closely associated with the heart, such as coronary arteries, valves, e.g. mitral valve, etc.

The term "nephrovascular tissue" refers to vascular tissue found in the kidneys of a host, e.g. renal arteries, etc.

The term "prothesis" as used herein refers to any device which is implanted into a mammal. The term includes heart valves and other heart components, vascular replacements or grafts, e.g. saphrenous vein grafts, artificial hearts, left ventricular assist devices, electrodes, and the like.

The term "valve" as used herein refers to a membranous fold in a canal or passage, which prevents the reflux of the contents of the contents passing through it.

The term "heart valve" or "cardiac valve" as used herein refers to a valve that controls the flow of blood to and from, as well as through, the heart, including the atrioventricular (e.g. the mitral valve), aortic, and pulmonary trunk valves.

The term "bioprosthetic heart valve" as used herein refers to an artificial cardiac valve composed of biological tissue of any mammal, which can be sterilized and mounted on a plastic or metal supportive structure.

The term "vessel" as used herein refers to any conduit in the circulatory system and includes arteries, arterioles, veins, venules, and capillaries.

The term "catheter" as used herein refers to any hollow, tubular device for insertion into a cavity, duct or vessel.

The term "ion exchanger" as used herein refers to a solid or liquid material containing ions that are exchangeable with other ions with a like charge that are present in solution in which the material is insoluble. The term "chelating agent" as used herein refers to an organic compound in which atoms form more than one coordinate bond with metals in solution. The term "ion exchange" as used herein refers to a chemical reaction in which a mobile hydrated ion of a solid are exchanged, equivalent for equivalent, for ions of like charge in a solution.

The term "fixation" or "fixing" as used herein refers to a process of treating biological material so as to preserve the material from natural decay, including decay by autolysis. Fixation includes methods such as exposing the biological material to glutaraldehyde or formaldehyde.

The term "acid" as used herein refers to a chemical substance that lowers the pH (increases the hydrogen concentration) when added to an aqueous solution. An acid can be inorganic or organic. The term "organic" acid as used herein refers to any acid the radical of which is a carbon derivative or a compound in which a hydrocarbon radical is united to COOH (a carboxylic acid) or to $SO_3H$ (a sulfonic acid). The term "inorganic" acid as used herein refers to any acid containing no hydrocarbon moiety. Acids can be "monobasic" wherein they have but one replaceable hydrogen atom and yield only one series of salts (e.g., HCl) or "polybasic" wherein they contain two or more hydrogen atoms which may be neutralized by alkalies and replaced by organic radicals.

The term "mineralization" as used herein refers to the deposition of an inorganic composition on a tissue or prosthesis, or the conversion of an organic compound to a simpler inorganic material. The term "calcification" as used herein refers to the deposition of an inorganic composition containing calcium on an organic composition. One example of calcification is the deposition of carbonated apatite on a tissue. Carbonated apatite is deposited as $Ca_{8.3}[PO_4]_{4.3}[CO_3]_x[HPO_4]_y[OH]_{0.3}$, where y decreases and x increases with increasing age, and x+y is a constant value of 1.7 (see Legaros, R., et al., 1987, Calcified Tiss. Int. 41:137–144).

The term "apatite" as used herein refers to a group of phosphate minerals that includes ten mineral species and has the general formula $X_5(YO_4)_3Z$, where X is usually $Ca^{2+}$ or $Pb^{3+}$, Y is $P^{5+}$ or $As^{5-}$, and Z is $F^-$, $Cl^-$, or $OH^-$. The term calcium apatite refers to a group of phosphate minerals where X is $Ca^{2+}$. The term "hydroxyapatite" refers to the minerals of the formula $Ca_5[PO_4]_3(OH)$.

The term "demineralization" as used herein refers to the removal by any means of an inorganic composition from a tissue or prosthesis. The inorganic composition can be solubilized, or can be removed in solid form, such as in the removal of individual or groups of crystals.

The term "decalcification" as used herein refers to the removal of an inorganic composition containing calcium from a tissue or prosthesis. One example of decalcification is the removal of hydroxyapatite from a tissue, such as a vessel. The inorganic composition containing calcium can be solubilized, or can be removed in solid form, such as in the removal of individual crystals or groups of crystals, e.g. calcified lesion debris.

The term "non-toxic" as used herein refers to a composition which does not cause undue damage to tissue during a treatment period.

The term "ultrasound" as used herein refers to sound waves having frequencies higher than those to which the human ear can respond (i.e., >16 kHz). The upper limit of ultrasonic frequency is one which is not sharply defined but usually taken to be 5 MHz for gases and 500 MHZ for liquids and solids (see Mason, T. J., and Lorimer, J. B., *Sonochemistry: Theory, Application, and Use of Ultrasound on Chemistry*, Chichester: Ellis Horwood, Oxford, 1988, herein incorporated by reference). The terms "low power ultrasound" and "high frequency ultrasound" as used herein refer to low amplitude (higher frequency) propagation. Low amplitude waves are typically used to measure the velocity and absorption coefficient of the wave in a medium in the 2 to 10 MHZ range. These waves are used, for example, in medical scanning, chemical analysis, and the study of relaxation phenomena.

The terms "high power ultrasound" and "low frequency ultrasound" as used herein refer to high energy waves known also as "power ultrasound" between 20 and 100 kHz which are used, for example, for cleaning, plastic welding, and to effect chemical reactivity.

The term "catheter based" as used herein refers to any minimally invasive procedure finding use in the cardiovascular system. Specific, non-limiting examples of a catheter based procedure include balloon angioplasty or percutaneous balloon aortic valvuloplasty (BAV).

The term "invasive procedure" or "open procedure" as used herein refers to any procedure with an open surgical field. One specific, non-limiting example of an invasive procedure is bypass surgery. Another specific, non-limiting example of an invasive procedure is intra-operative mechanical debridement (decalcification) of the aortic valve to treat aortic stenosis wherein the aorta is entered surgically (as in a valve replacement procedure) and the calcified deposits are removed using surgical tools or ultrasound.

DESCRIPTION OF THE SPECIFIC EMBODIMENTS

Methods and devices are provided for at least reducing the mineral content of a calcified lesion on vascular tissue. In the subject methods, the local environment of the calcified lesion is maintained at a subphysiological pH for a sufficient period of time for the desired amount of demineralization to occur, e.g. by flushing the lesion with a fluid capable of locally increasing the proton concentration in the region of the lesion. Also provided are catheters for performing the subject methods, where the catheters at least include a first lumen capable of delivering fluid to a vascular site and a second lumen capable of removing fluid from a vascular site, where the second lumen preferably has dimensions sufficient to allow passage of lesion debris. The subject methods find use in the treatment of vascular diseases characterized by the presence of calcified vascular tissue lesions. In further describing the subject invention, the methods will be discussed first followed by a description of the subject catheters that find use in performing the methods, as well as a discussion of systems comprising the catheters and kits for use in performing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The invention provides a method for at least reducing the mineral content of a vascular calcified lesion by contacting the lesion with a fluid capable of locally increasing the proton concentration in the region of the lesion. As used herein, the term "vascular calcified lesion" is used broadly to refer to any mineral containing formation that occurs on the surface of vascular tissue, usually on the inner surface of vascular tissue that is in contact with blood, e.g. the intima or inner wall of a blood vessel. Vascular tissue refers to any tissue that is present in the circulatory system of the host, as described above, and as such includes not only vessel tissue, such as arterial and veinous tissue, but also cardiac or heart tissue, including valves and other cardiovascular features or specialized tissue structures, e.g cardiovascular tissue. Vascular tissue also includes prosthetics that have been introduced into the host's cardiovascular system, including bioprosthetics, etc. In addition, vascular tissue includes the tissue of organs closely associated with the circulatory system, such as nephrovascular tissue found in the kidneys, and the like. The calcified lesion may be a substantially pure mineral deposit or coating over the surface of a region of vascular tissue, such as a coating or layer on at least a portion of valve tissue and the like, or may be a more complex formation that includes both mineral and other components, including organic matter, e.g. lipids, proteins, and the like.

The mineral component making up the calcified lesion is generally made up of one or more calcium phosphates, where the calcium phosphates are generally apatitic, specifically hydroxyapatite, carbonated hydroxyapatite (dahllite) and calcium deficient hydroxyapatite.

In addition to the mineral component, the lesion that is the target of the subject methods may also comprise one or more additional components, where such components include: lipids; lipoproteins; proteins; including fibrinogen, collagen, elastin and the like; proteoglycans, such as chondroitin sulfate, heparin sulfate, dermatans, etc.; and cells, including smooth muscle cells, epithelial cells, macrophages and lymphocytes. As such, calcified lesions that are targets of the subject methods include: type IV, type IV and type IV lesions, as defined in Stary et al., Arterioscler Thromb Vase Biol. (1995)15:1512–1531.

In arterial lesions that are targets of the subject methods, the mineral component of the calcified lesion generally makes up from about 10 to 100, usually from about 10 to 90 and more usually from about 10 to 85 dry weight % of the lesion. The size of the lesion that is the target of the subject methods varies depending on whether it is a lesion found in arteries, in the aorta or on a valve, e.g. a heart valve. As such, the size of the lesion may vary substantially, but will typically cover an area, e.g. surface of arterial intima, of at least about 1 $mm^2$, usually at least about 4 $mm^2$ and more usually at least about 10 $mm^2$, where the area covered by the lesion may be as large as 40 $mm^2$ or larger, but will usually not exceed about 20 $mm^2$, and more usually will not exceed about 15 $mm^2$.

As summarized above, the mineral content of vascular lesions is reduced according to the subject invention by maintaining the local environment of the lesion at a subphysiological pH for a sufficient period of time for the desired amount of demineralization to occur. By local environment of the lesion is meant the immediate vicinity of the lesion, such as the area defined by a set distance from any surface point (i.e. point not adjacent or juxtaposed to the vesicular tissue, e.g. intima, with which the lesion is associated) on the lesion, typically extending at least 1 $mm^2$, usually at least 2 $mm^2$ beyond the area covered by the lesion. For example, where the target lesion covers a 4 $mm^2$ surface of arterial intima, the local environment will extend to cover an area of 6 $mm^2$. In three-dimensional terms, where a lesion occupies a volume of 8 $mm^3$, the volume of the local environment will be at least 9 $mm^3$ and will often be larger. In many embodiments, the local environment may extend beyond this limited area. For example, the local environment may be mechanically isolated section of a vessel or valve in which the lesions are present, where the volume of such an isolated section may range from about 4 to 4000 $mm^3$, usually from about 40 to 2000 $mm^3$ and more usually from about 100 to 1000 $mm^3$. Typically, the volume of the local environment of the lesion ranges from about 1 to 100, usually from about 5 to 50 and more usually from about 10 to 20 fold greater than the volume of the lesion, where the local environment volume includes the volume of the lesion. Importantly, however, the local region does not include the entire vascular system or even a fraction thereof. As such, the local environment of lesion is less than 90%, usually less than 80% and more usually less than 50% of the entire volume (e.g. the volume of circulating blood) of the vascular system of the host or subject being treated. In many embodiments, the local environment is less than 5% and typically between about 1 to 2% of the entire volume of the vascular system of the host.

As mentioned above, the pH in the local environment is maintained at a subphysiological level for a sufficient period of time for the desired amount of demineralization to occur. Typically, the pH is maintained at a value that does not exceed about 5 and usually does not exceed about 4, but generally does not fall below about 1 and usually does not fall below about 2. Within the above range, the pH may be constant or variable over the course of the demineralization procedure, i.e. over the period of time during which the pH of the local environment is maintained at a subphysiological value.

The time period during which the local pH is maintained at a subphysiological level in the local region of the lesion is sufficient for the desired amount of demineralization to occur. As such, the pH of the local environment is maintained a suphysiological value for a period of time ranging from about 5 to 200 minutes, usually from about 10 to 100 minutes and more usually from about 10 to 30 minutes.

The pH of the local environment in the region of the lesion may be maintained at the requisite subphysiological level using any convenient protocol. Of particular interest in many embodiments is the use of a dissolution solution that is introduced into the local environment of the lesion and is capable of locally increasing the proton concentration in the local environment of the lesion. By capable of locally increasing the proton concentration is meant that the dissolution solution, upon introduction into the local environment of the lesion, as described in greater detail below, is capable of increasing the hydrogen ion concentration or [H$^+$] in the region of the lesion. In other words, the solution is capable of reducing the pH in the region of the lesion to the requisite subphysiologic level.

A variety of different types of dissolution solutions may be employed in the subject methods, as long as the solutions are capable of increasing the proton concentration locally in the region of the target lesion to the desired subphysiologic level. In other words, any solution that is capable of providing the requisite subphysiologic pH in the local environment of the lesion is suitable for use in the subject methods.

One type of solution that finds use is an acidic dissolution or treatment solution. The extent to which the delivery system that is employed in the method (described in greater detail below) can isolate the mineralized lesion will determine the nature and composition of the acidic treatment solution, at least to some extent. For example, where a delivery device is employed that is capable of substantially isolating the local environment of the lesion, a more stringent acidic treatment solution might be employed, e.g. an acidic treatment solution with a low pH. In addition, the means by which the solution is introduced into the environment of the lesion, e.g. the rate of flow of the acidic treatment solution over the mineralized lesion where the solution is administered by flushing, can determine the nature and composition of the acidic treatment solution. In general, an acidic treatment solution can be used at any concentration that does not cause undue tissue damage under the conditions of use. Tissue damage can readily be assessed by one of ordinary skill in the art. For example, tissue treated with the acidic treatment solution can be examined microscopically for evaluation.

The acidic treatment solution will generally have a pH of less than about 6.5 and more than about 1.0, where the pH is usually less than about 4.0 and more than about 1.0. The acidic treatment solution can be an inorganic or organic acidic treatment solution. Suitable inorganic acids include halogen acids, oxy acids and mixtures. Specific inorganic acids of interest include, but are not limited to, hydrochloric, nitric, sulfuric, phosphoric, hydroboric, hydrobromic, carbonic and hydroiotic acids. For an inorganic acid, the acid can be a concentrated acid, or can be diluted. Upon dilution, the concentration of an inorganic acid will generally be from about 10 N to about 0.01 N, preferably between 5 N to 0.1 N. Organic acids, i.e. acids that include a hydrocarbon moiety) for use with the subject invention include, but are not limited to, any organic acid of one to six ($C_1$ to $C_6$) carbons in length. Organic acids include, but are not limited to, formic, acetic, propionic, maleic, butanoic, valeric, hexanoic, phenolic, cyclopentanecarboxylic, benzoic acids, and the like. For an organic acid, the acid can be in concentrated form, or can be diluted. The acidic treatment solution can be composed of either a monobasic or a polybasic acid.

In a particularly preferred embodiment, the solution that is employed is a carbonic acid solution. Carbonic acid solutions that find use are aqueous solutions that have a pH that is sufficiently low to achieve the desired subphysiological pH in the local region of the lesion during treatment. As such, the pH of the carbonic acid solution is typically less than about 6, usually less than about 5 and more usually less than about 4, where the pH may be as low as 2 or lower, but will generally not be below about 1. The carbonic acid concentration of the solution may vary, but will generally range from about 0.1 to 4.0 M and usually from about 0.1 to 1.0 M. The carbonic acid solution should be bubble free, i.e. $CO_2$ bubble free, during use. As such, the pressure and/or temperature of the carbonic acid solution may be modulated to provide the requisite bubble free properties. The carbonic acid solution may be at ambient or elevated pressure, i.e. pressurized. Where the carbonic acid solution is pressurized, it will be pressurized to at least about 10 bar (10 atm), usually at least about 50 bar and more usually to at least about 100 bar, where it may be pressurized to a pressure of 1000 bar or greater. The temperature of the carbonic acid solution may vary from about 0 to 37° C., usually from about 10 to 37° C. and more usually from about 20 to 37° C.

The carbonic acid solution may be produced in a number of different ways. For example, the carbonic acid solution may be prepared by combining sodium bicarbonate and hydrogen chloride solutions in a manner sufficient to produce a carbonic acid solution. The sodium bicarbonate solution that is employed will generally have a sodium bicarbonate concentration ranging from about 0.01 to 1.0 M, and usually from about 0.02 to 0.1 M. The hydrogen chloride solution that is employed will have a concentration ranging from about 0.01 to 1.0 M and usually from about 0.01 to 0.5 M. Upon combination of the sodium bicarbonate solution and hydrogen chloride solution, carbonic acid is produced in accordance with the following equilibrium equation:

The equilibrium of the above reaction is maintained in favor of production of the proton by maintaining the pressure and temperature of the solution at appropriate values. For a solution prepared in this manner, the pressure of the solution is maintained in a range of from about 10 to 200 bar and usually from about 50 to 150 bar while the temperature is maintained at a value ranging from about 0 to 37° C. and usually from about 20 to 37° C.

The carbonic acid solution that finds use in the subject invention can also be produced by making an aqueous solution that is saturated with respect to $CO_2$. In this embodiment, the solution is maintained as bubble free, by which is meant that $CO_2$ gas is prevented from coming out of solution such that the carbonic acid equilibrium reaction:

is driven in the direction of carbonic acid, i.e. $H_2CO_3$, and consequently proton and bicarbonate ion production. Generally, the $pCO_2$ in this carbonic acid solution is at least about 100, usually at least about 500 and more usually at least about 1000 mmHg, where the $pCO_2$ of the solution may be as high as 5000 mmHg or higher, but will generally not exceed about 10,000 mmHg. The solution prior to delivery will typically be pressurized to some pressure above atmospheric pressure such that it remains bubble free and yet saturated, even supersaturated, with respect to the $CO_2$. As such, the pressure of the solution is generally at least about 10 bar, usually at least about 50 bar and more usually at least about 100 bar, where the pressure may be as high as 200 bar or higher, but will generally not exceed about 1000 bar. The temperature of the solution may also be modulated to obtain the desired dissolved $CO_2$ in the solution. As such, the temperature may range from about 0 to 37° C., usually from about 10 to 37° C. and more usually from about 20 to 37° C. A variety of technologies are known to those of skill in the art for producing aqueous solutions that are saturated with respect to $CO_2$, any of which may be employed to produce the carbonic acid solution finding use in the subject methods. Of particular interest are the techniques disclosed in U.S. Pat. Nos. 5,086,620; 5,261,875; 5,407,426; 5,599,296; 5,569,180; 5,693,017; 5,730,935; 5,735,934; and 5,797,874; the disclosures of which applications are herein incorporated by reference. Briefly, a stable, bubble-free saturated $CO_2$ aqueous solution is produced by contacting gaseous $CO_2$ with an aqueous carrier medium, e.g. pure water, under elevated pressure conditions such that the gaseous $CO_2$ goes into, and is maintained in, solution.

The dissolution solutions employed in the subject invention may also comprise one or more additional components that serve a variety of purposes. Components that may be included are ions which serve to: (a) prevent apatite formation, (b) prevent apatite reformation, (c) modify apatite solubility, etc., where such ions include $Mg^{2+}$, $Na^+$ and the like. When present, the concentration of the magnesium ion in the solution will generally range from about 0.01 to 0.20 M, usually from about 0.05 to 0.1 M.

The solution may further include an oxygenating medium for delivery of oxygen to the local environment of the lesion during treatment, i.e. the solution may further comprise oxygen—the solution may be supersaturated with respect to $O_2$. When present, the solution will comprise 1 to 4, usually 1 to 3 ml $O_2$/g fluid. Any convenient oxygenating medium may be employed, including the hyperbaric oxygen mediums disclosed in U.S. Pat. Nos. 5,086,620; 5,261,875; 5,407,426; 5,599,296; 5,569,180; 5,693,017; 5,730;935; 5,735,934; and 5,797,874, the disclosures of which are herein incorporated by reference. An example of situations where oxygenating mediums find use in the dissolution solution include the treatment of diffuse arterial lesions by the subject methods, e.g. diffuse arterial lesions found in the limbic extremities. For example, to treat a lower limbic extremity diffuse arterial lesion, e.g. an arterial lesion present below the knee, one can produce an isolated local environment by blocking the appropriate artery (e.g. posterior tibial artery, anterior tibial artery) and vein (e.g. great saphenous vein, small saphenous vein) on either side of the diffuse lesion. The lesion can then be contacted, e.g. flushed, with the dissolution solution comprising the oxygenating medium by introducing the solution into the artery and removing it from the vein, as described in greater detail below. In this embodiment, the entire circulatory system below the substantially blocked portions of the artery and vein is transformed into the local environment of the lesion in which a subphysiologic pH is maintained. The oxygenating medium serves to maintain the requisite oxygen levels in the tissue of the local environment of the lesion.

The dissolution treatment solution can further include calcium-chelating agents, for example, EDTA, crown ethers, and the like. The concentration of these agents will vary, but will generally not exceed about 4.0 M and usually will not exceed about 1.0 M.

The dissolution solution may also include an enzymatic component that serves to promote the formation of protons in the solution and local environment of the lesion in order to provide for the subphysiologic pH. A variety of enzymes or activities may be employed, depending on the specific nature of the dissolution solution. For example, in those embodiments in which the dissolution solution is saturated with $CO^2$ gas, the solution can further include carbonic anhydrase. The enzyme may be a naturally occurring enzyme or synthetic homologue thereof, where the enzyme may be produced via purification from naturally occurring sources or through recombinant technology.

In addition, the dissolution solution may further include one or more components which act on the non-mineral phase of the target lesion in order to disrupt the lesion and promote its disruption and/or dissolution. Such, organic disruption/dissolution agents that may be present in the dissolution solution include: surfactants e.g. TWEEN™, detergents, oxidants; thrombolytic agents, e.g. urokinase, tPA, etc.; enzymes, e.g. proteases, collegenases; heparin; cholesterol diluting agents (see U.S. Pat. No. 4,423,725, the disclosure of which is herein incorporated by refernece)etc.

In the subject methods, the dissolution solution is introduced into the local environment of the lesion in a manner sufficient to maintain the local environment of the pH at the requisite subphysiological level for a sufficient period of time for the desired amount demineralization to occur. As such, the subject methods generally involve contacting the lesion with the dissolution solution. The manner in which contact is achieved may be static or dynamic. By static is meant that a predetermined amount of dissolution solution is introduced into the local environment of the lesion and maintained in the local environment of the lesion for the entire treatment period, without the addition of further quantities of dissolution solution. By dynamic is meant the dissolution solution is introduced into the local environment of the lesion one or more times, including continuously, during the treatment period.

During the dissolution procedure, protons from the local environment are removed as a result of the demineralization process. As such, it is often desirable to introduce the dissolution solution into the local environment of the lesion in a dynamic manner. Dynamic introduction of the dissolution solution typically involves flushing the lesion with the dissolution solution, where flushing involves a continuous flow of the dissolution solution across the surface of the lesion. In other words, the dissolution fluid is continuously flowed through the local environment of the lesion for the period of time required for the desired amount of demineralization to occur. Simultaneously, fluid is removed from the local environment of the lesion such that the overall volume of fluid in the local environment of the lesion remains substantially constant, where any difference in volume at any two given times during the treatment period does not exceed about 50%, and usually does not exceed about 10%. Where the lesion is flushed with the dissolution solution, the flow rate of the dissolution solution through the local environment of the lesion is generally at least about 1 volume/minute, usually at least about 2 volumes/minute and more usually at least about 10 volumes/minute, where the flow rate may be as great as 100 volumes/minute or greater, but usually does not exceed about 1000 volumes/minute and more usually does not exceed about 500 volumes/minute, where by "volume" is meant the local environment of the lesion.

When treatment involves dynamic flushing of the local environment of the lesion, the total amount of dissolution fluid that is passed through the local environment of the lesion during the treatment period typically ranges from about 1 to 500 liters, usually from about 10 to 200 liters and more usually from about 50 to 100 liters. In contrast, where a static methodology is employed, the total amount of dissolution fluid that is introduced into the local environment of the lesion ranges from about 100 ml to 1 liter, and usually from about 100 to 500 ml.

Any convenient means may be employed for introducing the dissolution solution into the local environment of the lesion. For example, for introduction of the dissolution fluid into the coronary arteries for treatment of lesions positioned thereon, a catheter apparatus (see e.g, U.S. Pat. Nos. 5,167, 628, 4,850,975, the disclosures of which are incorporated by reference) can be utilized, as can any of the assemblies described below. The method of the invention can further be utilized during invasive procedures, such as during cardiopulmonary bypass. The method can be utilized with partitioning devices, such as the device described in U.S. Pat. No. 5,702,368, the disclosure of which is herein incorporated by reference. Where the device includes a means for substantially isolating the local environment of the lesion, the subject method further comprises a step of substantially isolating the local environment of the lesion from the remainder of the subject's circulatory system.

Maintenance of the local environment of the calcified lesion at a subphysiologic pH, as described above, results in at least partial demineralization of the lesion, i.e. at least a reduction of the calcium phosphate content of the lesion. By reduction is meant that the total overall dry weight of calcium phosphate mineral is reduced or decreased, generally by at least about 50%, usually by at least about 75% and more usually by at least about 90%. In certain embodiments, substantially all of the calcium phosphate content of the lesion may be removed, where by substantially all is meant at least about 90%, usually at least about 95% and preferably at least about 99% dry weight of the original calcium phosphate present in the lesion is removed.

The above methodology using a single dissolution solution can be modified in a number of different ways to achieve particular results. Thus, instead of using a single dissolution solution, a plurality of different dissolution solutions which vary by one or more parameters (e.g. type, pH, concentration etc.) may be sequentially introduced into the region of the lesion. In such embodiments, the number of different dissolution solutions employed is at least 2, but generally does not exceed about 4 and usually does not exceed about 3.

In addition to the use of a dissolution solution(s), the subject methods may further involve the use of the priming solution, which serves to prepare the local environment of the calcified lesion for treatment in a desired way. For example, it may be desirable to remove blood from the local environment of the lesion prior to introduction of the dissolution solution. Examples of priming solutions that may find use in these embodiments include: water for injection, saline solutions, e.g. Ringer's, or other physiologically acceptable solutions. A priming solution that comprises an oxidizing agent may be employed to remove organic coatings from the mineralized lesion and thereby expose the mineral portion of the lesion. Thus, the priming solution may also be used to remove acid insoluble organic matter that might shield the mineralized deposit from the acidic treatment solution. The priming solution can also contain chelating agents. In one embodiment, the priming solution is a basic solution. The basic solution can be composed of any inorganic or organic base. The basic solution can be concentrated base, or can be a dilute basic solution. The pH of the basic is solution is generally greater than about 9.0. In one embodiment, the basic solution is between a pH of about 10.0 and about 12.0. The basic solution can be a solution of an inorganic base. In one embodiment, the basic solution is a solution of sodium hydroxide (NaOH). In one embodiment, the basic solution is a dilute solution of sodium hypochlorite.

In certain embodiments, it is desirable to rinse or wash the local environment of the lesion following treatment with the dissolution solution. The rinsing solution can be any solution sufficient to remove or dilute the acidic treatment solution from the vascular tissue, thereby reducing the acidity in the local environment of the lesion. In one embodiment, the rinsing solution is a neutral solution. The neutral rinsing solution can be a buffered solution of physiological pH. Preferably, the neutral rinsing solution has a pH of about 7.0 to about 8.0. More preferably, the neutral rinsing solution has a pH of about 7.4. One non-limiting example of a neutral rinsing solution is phosphate buffered saline.

In certain embodiments, it is of interest to further treat the local environment of the lesion, i.e. which may or may not comprise any of the originally present lesions depending on the particular method conducted, with one or more agents that serve to inhibit the formation of the new calcified lesion on the vascular tissue on which the lesion was present. Inhibition agents that may be employed include: water-soluble phosphate esters (e.g., sodium dodecyl hydrogen phosphate, as described in U.S. Pat. No. 4,402,697, the disclosure of which is herein incorporated by refernece); water soluble quaternary ammonium salts (e.g., dodecyltrimethyammonium chloride, as described in U.S. Pat. No. 4,405,327, the disclosure of which is herein incorporated by reference); sulfated higher aliphatic alcohols (e.g., sodium dodecyl sulfate, as described in U.S. Pat. No. 4,323,358, the disclosure of which is herein incorporated by reference); agents that result in the covalent coupling of aliphatic carboxylic acids (as described in U.S. Pat. No. 4,976,733, the disclosure of which is herein incorporated by reference); and the like.

In certain embodiments, external energy is applied to the target lesion to promote mechanical break-up of the lesion into particles or debris that can be easily removed from the site of the lesion. Any means of applying external energy to the lesion may be employed. As such, jets or other such means on a catheter device which are capable of providing varying external forces to the lesion sufficient to cause the lesion to break up or disrupt may be employed. Of particular interest in many embodiments is the use of ultrasound. The ultrasound can be applied during the entire time of contact of the cardiovascular tissue with the acidic treatment solution, or the ultrasound can be applied for only part of the treatment period. In one embodiment, ultrasound is applied for several short periods of time while the dissolution treatment solution is contacted with the cardiovascular tissue. There are several devices for the application of ultrasound to cardiovascular tissue known to those of skill in the art. For example, U.S. Pat. No. 4,808,153, the disclosure of which is herein incorporated by reference, describes an ultrasound apparatus to be used in an artery without damaging the artery, and U.S. Pat. No. 5,432,663, the disclosure of which is herein incorporated by reference, describes an apparatus for generating ultrasonic energy useful for removal of intravascular blockages. The ultrasound can be low frequency ultrasound.

In such methods where external energy is applied to the lesion in order to disrupt or break-up the lesion into particles or debris, the particles or debris may range in size from about 0.01 to 4.0 mm, usually from about 0.1 to 2.0 mm and more usually from about 0.5 to 1.0 mm. In such instances, the method may further include a step in which the resultant particles are removed from the local environment of the lesion. Particles may be removed from the local environment of the lesion using any convenient means, such as the catheter of the subject invention described in greater detail infra.

In addition, it may be convenient to monitor or visualize the lesion prior to or during treatment. A variety of suitable monitoring means are known to those of skill in the art. Any convenient means of invasive or noninvasive detection and/or quantification may be employed. Such means include plain film roentgenography, coronary arteriography, fluoroscopy, including digital substraction fluoroscopy, cinefluorography, conventional, helical and electron beam computed tomography, intravascular ultrasound, magnetic resonance imaging, transthoracic and transesophageal echocardiography, rapid CT scanning, and the like. Any of these means can be used to monitor the reduction in mineralization by the method of the invention. The noninvasive techniques most commonly used in practice, and of use to monitor demineralization of cardiovascular tissue by the method of the subject invention, include conventional and digital fluoroscopy and computed tomography, such as electron beam computed tomography (EBCT) (Reinmuller, R., and Lipton, M. J., *Dynam. Cardiovasc. Imaging* 1:139–145, 1987). A quantitative scoring system has been designed for use with EBCT (Agatston, AS, et al., *J. Am. Coll. Cardiol.* 15:827–832, 1990; Janowitz, W. R., et al., *Am. J. Coll. Cardiol* 68:1–6, 1991). Cinefluorograph and IVUS are commonly used by to evaluate calcification in specific lesions before invasive procedures, such as during cardiac catheterization (Friedrich, G. J., et al., *Am. Heart J.* 128:435–441, 1994; see also Yock et al., Intravascular Ultrasound, Scientific American Science & Medicine (September/October 1995) 2:68–77). In addition, transthoracic echocardiography is very sensitive to detection of mitral and aortic valve calcification. (Fernandes, F., et al., *Circulation* 88:2532–2540, 1993).

The subject methods find use in a variety of different applications in which it is desired to at least reduce, if not substantially remove, at least the mineral component of a calcified lesion. One application in which the subject methods find use is in the treatment of a host suffering from a vascular disease associated with the presence of vascular calcified lesions. Such vascular diseases include diseases in which one or more different calcified lesions are present on one or more locations of the vascular tissue of the host, where the lesion(s) may be present on a vessel wall, on a valve, etc.

By treatment is meant at least a reduction in a parameter of the disease, where parameter may include typical symptoms indicative of occluded vessels or malfunctioning valves, e.g. chest pains, angina etc., or risk factors associated with the disease or condition, e.g. narrowing of arteries, and the like. Treatment also includes situations where the host is cured of the vascular disease, i.e. where the lesion is completely removed.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the hosts will be humans.

Also provided by the subject invention is a catheter device particularly suited for use in the subject methods. A critical feature of the subject catheters is that they include at least one fluid introduction means for introducing a dissolution fluid to the local environment of the lesion and a fluid removal means for removing fluid from the local environment of the lesion. The catheter devices of the subject invention also typically include a means for isolating the local environment of the target lesion.

The dissolution fluid introduction means is generally a lumen having a proximal end in fluid communication with the dissolution fluid source, e.g. dissolution fluid reservoir, and an open distal end capable of being introduced into the local environment of the target lesion. By "lumen" is meant an elongated vessel having a tubular structure having a proximal and distal end, where the cross-sectional shape along the length of structure is generally circular, ovoid or some other curvilinear shape. The dissolution fluid introduction lumen has sufficient dimensions to allow for the desired flow rate at the site of the target lesion. However, in those embodiments in which a pressurized dissolution fluid is delivered to the local environment of the lesion, the dimensions are often sufficient to reduce bubble formation, e.g. $CO_2$ bubble formation. As such, the dissolution fluid introduction lumen has an inner diameter (ID) that is at least about 50 $\mu$m, usually at least about 100 $\mu$m and more usually at least about 200 $\mu$m, where the inner diameter will typically not exceed about 2000 $\mu$m and usually will not exceed about 1000 $\mu$m. Depending on the configuration of the catheter device, the entire cross-sectional area may be available for fluid flow, or a portion of the cross-sectional area may be occupied by one or more additional device elements, e.g. a guide wire, one or more additional lumens, and the like, as described in greater detail infra. The fluid introduction lumen may be fabricated from a wide variety of materials. See the patents listed in the relevant literature section, supra. In those embodiments where the dissolution fluid is pressurized, as described above, the lumen is fabricated from materials capable of preserving the pressure of the fluid. Such materials are described in U.S. Pat. Nos. 5,599,296; 5,569,180; 5,693,017; 5,730,935; 5,735,934; and 5,797,874; the disclosures of which applications are herein incorporated by reference. Also of interest are multiple small lumens having ID of between about 50 and 80 $\mu$m, usually around 75 $\mu$m.

In addition to the fluid introduction means, the subject catheters further comprise a fluid removal means capable of removing fluid from the local region or environment of the lesion. A critical feature of the fluid removal means is that it is capable of removing fluid from the local environment of the lesion at the same rate as that at which fluid is introduced into the local environment of the lesion by the dissolution fluid introduction means. The fluid removal means is typically a lumen having dimensions that allow for adequate fluid flow from the local environment of the target lesion. In addition, in preferred embodiments the dimensions of the second lumen are such that they allow passage of the debris from the local environment of the lesion through the second lumen. In such embodiments, the fluid removal lumen has an inner diameter that is substantially longer than the inner diameter of the fluid introduction lumen, where by substantially longer is meant at least about 2 fold longer, usually at least about 5 fold longer. As such, the fluid removal lumen typically has an inner diameter that is at least about 1 mm, usually at least about 2 mm and more usually at least about 3 mm, where the inner diameter typically does not exceed about 5 mm and usually does not exceed about 4 mm. The fluid removal lumen may be fabricated from any suitable material, where a variety of suitable materials are known to the those of skill in the art.

In many embodiments, the subject device further preferably includes a means for substantially isolating the local environment of the lesion from the remainder of the host's circulatory system. By substantially isolating is meant that fluid communication between the local environment of the lesion and the remainder of the host's circulatory system is essentially removed—i.e. the local environment of the lesion is no longer accessible by fluid from the remainder of the host's circulatory system or vice versa. Any convenient means may be employed for isolating the local environment of the lesion. Such means include "cup" components that snugly fit over the lesion and thereby isolate it from the remainder of the circulatory system, dual balloon systems that inflate on either side of the lesion to isolate the local environment, etc.

In addition to the above components, the capillary devices of the subject invention may further include: (a) one or more additional lumens, e.g. for introducing a rinse or wash fluid to the local environment of the lesion; a means for allowing blood to flow through the isolated local environment, e.g. a pass through lumen; a means for applying energy to the lesion, e.g. an ultrasonic means; and visualization or monitoring means; etc.

All of the above components are conveniently present in a catheter device capable of accessing the cardiovascular site of interest. The catheter device will be capable of operatively communicating with other components and devices necessary for operation of the catheter, such as fluid flow means, fluid reservoirs, power means, pressurized gas supply means, and the like.

Figure 1:
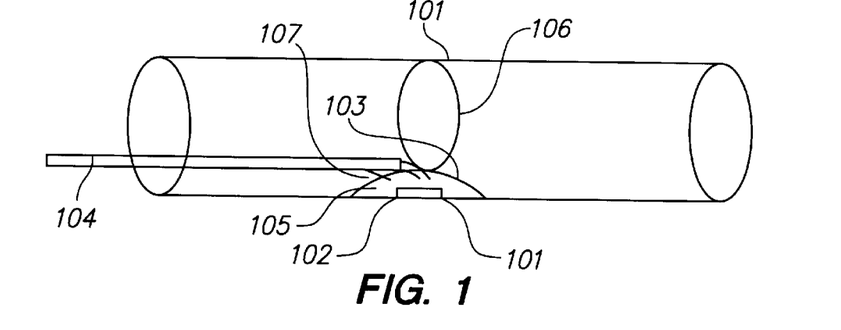
FIG. 1 is a perspective view of a single-cup catheter assembly of the invention.

The subject devices will now be described further in terms of representative embodiments as shown in the figures. FIG. 1 shows an assembly designed for use in connection with the present invention. A schematic view is shown. The assembly is designed for use in minimally invasive procedures, and in an open surgical field. The assembly is shown in a blood vessel having walls 101 and a mineralized area 102. Catheter 104 has a flexible cup 103 secured near the distal end of the catheter. In one embodiment, the cup can be folded for insertion into the vessel, and then expanded at the desired location in the vicinity of the mineralized area. A defined area 105 is created by the contact of the cup 103 with the vessel wall 101. The catheter is designed to allow infusion of the area 105 with an acidic treatment solution. The catheter is composed of flexible tubing such that it can be situated at any position along a vessel, and should be sufficiently strong so that it withstands the pressure created from the both the flow of the acidic treatment solution and the suction generated during the removal of the acidic treatment solution. Cup 103 can be held in place by maintaining the pressure within area 105 sufficiently below blood pressure, or optionally by a balloon 106 or other means. An ultrasound probe 107 is used to generate ultrasonic energy.

In one embodiment, the catheter 104 is a single lumen catheter. The lumen of the catheter communicates with the interior of the flexible cup 102. An acidic treatment solution can be applied through the catheter to the defined area 105 for the desired time period. Following this time period, the cup is removed, and the acidic treatment solution is allowed to disperse. Alternatively, a device to create suction can be applied to the more proximal end of the catheter so that the acidic treatment solution is drawn away from the defined area via the single lumen. Similarly, following treatment with the acidic treatment solution the rinsing agent can be applied through the single-lumen catheter if desired.

In another embodiment, the catheter 104 is a double-lumen catheter, both of which communicate with the interior of the flexible cup 102. One of the lumens allows the infusion of either an acidic treatment solution or a rinsing solution. The second lumen removes the acidic treatment or rinse solution. Infusion and suction can be alternated, or the two process can be applied simultaneously to create a flow of solution.

In yet another embodiment, catheter 104 is a triple-lumen catheter, all of which communicate with the interior of flexible cup 102. In this embodiment, one of the lumens allows the infusion of an acidic treatment solution, one of the lumens allows the infusion of a rinsing solution, and one of the lumens allow for the application of suction for the removal of solution.

Figure 2:
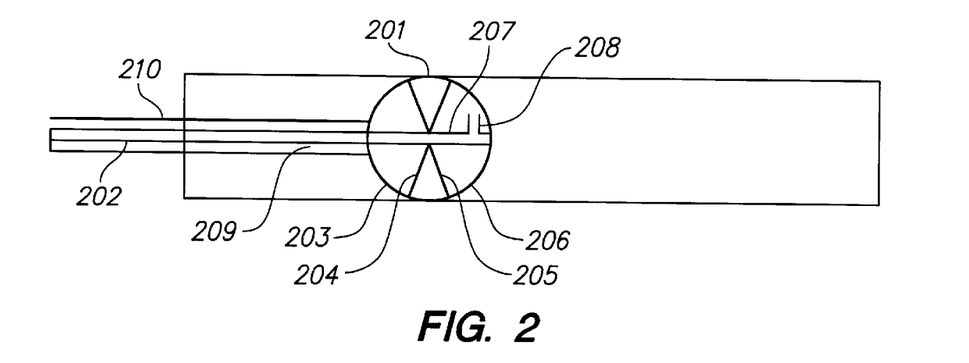
FIG. 2 is a perspective view of a double-cup catheter assembly of the invention.

Referring to FIG. 2, a double cup assembly for use with the present invention is shown. The assembly is designed for use in minimally invasive procedures and in an open surgical field. In this apparatus, a first lumen 209 of double lumen inlet catheter 202 is operatively connected to a cup for the application of solution 203. Lumen 209 of the catheter 202 terminates at this first cup 203. This first cup 203 is placed in close proximity to one side 204 of a valve 201 or another projecting structure. One lumen of the catheter 207 passes through the opening of the valve 201, as is terminates at second cup 206. Lumen 207 can be positioned independently of lumen 209 by a guidewire 210. This second cup 206 is placed in close proximity to the on the opposite side 205 of the valve 201 than the first cup 203. In addition, at least one outlet 208 is located on the second lumen of the catheter between the opposing side of the valve 205 and the second cup. An infusion means is attached to the first lumen 209 of the catheter so that acidic treatment solution is delivered to one side 204 of the valve. A removal means is attached to the second lumen 207 of the catheter so that the acidic treatment solution is removed from the opposite side 205 of the valve. Alternatively the infusion means can be attached to the second lumen 207 and the removal means can be attached to the first lumen 209. The solution is preferably applied to the side of the valve opposite the side to be to be treated, and is removed from the demineralized (treated) side. Both lumens of the catheter 202 and 205 are formed of flexible tubing such they can be situated in an appropriate position in close proximity to the valve, and are sufficiently strong to withstand the pressure created from the flow of the acidic treatment solution or the suction generated during the removal of the acidic treatment solution.

Figure 3:
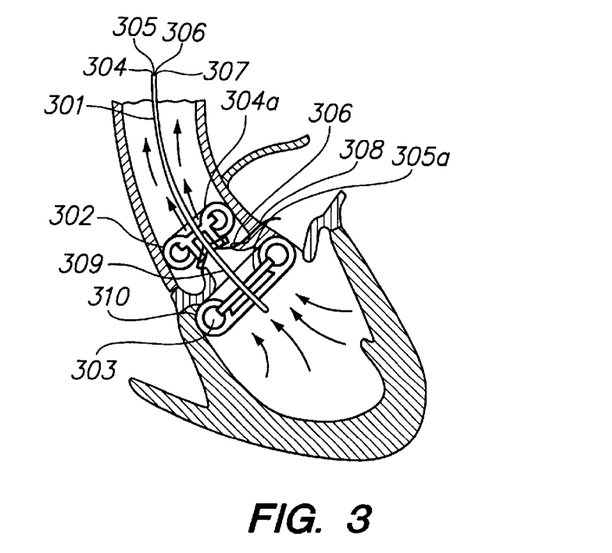
FIG. 3 is a perspective view of a double-balloon catheter assembly of the invention.

Referring to FIG. 3, a balloon catheter assembly of the present invention is shown. The assembly is designed for use in minimally invasive procedures or in an open surgical field. The balloon catheter assembly includes a four lumen catheter 301 having two toroid (doughnut)-shaped balloons 302 and 303 attached in series at a distance apart the catheter 301. The catheter 301 terminates just beyond the second balloon 303. The catheter has four lumens 304, 305, 306, and 307. The first lumen 304 communicates with the interior of the first balloon 302 through a lumen branch 304a. Thus, the first balloon can be inflated and deflated by applying positive and negative pressures through lumen 304. The second lumen 305 communicates with the interior of the second balloon 303 though a lumen branch 305a. Thus, the second balloon can be inflated and deflated by applying positive and negative pressure through lumen 305. Lumen 306 is used for the infusion of the acidic treatment solution or the rinsing solution and can open anywhere in the defined area between the two balloons 302 and 303. Lumen 306 can open at one endpoint 308, as shown, or can have multiple branches, each of which open an one endpoint. In the embodiment shown, lumen 306 has one endpoint opening 308 at the inner surface of the first balloon. However, other embodiments can be envisioned, such as one or more opening(s) at sites on region of the catheter between the two balloons 309. Lumen 307 is used for the removal of the acidic treatment solution or the rinsing solution, and can open anywhere in the defined area between the two balloons 302 and 303. Lumen 307 can open at one endpoint 310, as shown, or can have multiple branches, each of which open at one endpoint. In the embodiment shown lumen 307 has one endpoint opening 310 at the inner surface of the second balloon. However, other embodiments can be envisioned, such as one or more opening(s) at sites on the catheter between the two balloons 309.

Also provided by the subject invention are systems for use in performing the subject methods. The systems of the subject invention at least comprise components necessary for the using the above catheters in the subject methods. As such, the systems at least include a dissolution fluid reservoir capable holding or storing the dissolution fluid just prior to administration to the local environment of the lesion. In addition, the subject systems will include a means for moving the dissolution fluid through the fluid introduction means to the local environment of the lesion, where such means is typically a pump. The system may also conveniently include a means for maintaining the pressure and/or temperature of the dissolution fluid at a desired value. In addition, the subject systems include a means for removing fluid from the local environment of the lesion, e.g. a second pumping means or suction means. The above elements of the subject system may conveniently be present in housing fabricated of a suitable material.

Also provided are kits for use in performing the subject methods. The kits typically comprise at least the dissolution fluid to be used in the subject methods, such as a carbonic acid solution, as described above, where the solution may be present in a pressurized and/or climate controlled container so as to preserve the stability of the dissolution solution. For kits that are to be used in methodologies in which the fluid is flushed through the local environment of the lesion, the amount of dissolution fluid present in the kit ranges from about 1 to 500 liters, usually from about 10 to 200 liters and more usually from about 50 to 100 liters. For kits that are to be used in static methodologies, the amount of dissolution fluid present in the kit generally ranges from about 100 ml to 1 liter and usually from about 100 ml to 500 ml. Alternatively, the kit may comprise precursors of the dissolution solution for use in preparing the solution at the time of use. Also present in the kit may be a catheter for use in performing the subject methods, particularly a catheter according to the present invention. In addition to the dissolution fluid or precursors thereof, the kit may further comprise one or more addition fluids, such as a priming solution, a washing solution, and the like. Finally, the kits will include instructions for practicing the subject methods, where such instructions may be present on one or more of the kit components, the kit packaging and/or a kit package insert.

The following examples are offered by way of illustration and not by way of limitation.

EXPERIMENTAL

Example 1

Human Aortic Valve Tests in vitro

Calcified aortic heart valves are removed operatively during valve replacement surgery and used as an in vitro test system to optimize methods of demineralization. For these studies, a comparison of different acidic treatment solutions is performed. In addition, the acidic treatment solutions are contacted with the calcified aortic valves for varying periods of time. The following solutions and conditions are examined: 0.1 M HCl, 1.0 M HCl, concentrated HCl, 0.1 M HCl+0.01 M EDTA, 1.0 M HCl+0.01 M EDTA, concentrated HCl+0.1 M EDTA, 0.1 M $H_2SO_4$, 1.0 M $H_2SO_4$, 0.1 M $H_2SO_4$+0.01 M EDTA, 1.0 M $H_2SO_4$+0.1 M EDTA, 1.0 M formic acid, concentrated fromic acid, 1.0 M formic acid+0.1 M EDTA, 1.0 M acetic acid, concentrated acetic acid, 1.0 M acetic acid and 0.1 M EDTA, 1.0 M succinic acid, 1.0 M succinic acid+0.1 M EDTA.

Explanted valves are weighed after thorough washing. A flow through system comprising the valves are then prepared and each solution is flowed through the explanted valve. Weight loss is measured at 5, 10, 30, 60, 90 and 120 minutes of incubation in the acidic treatment solution. This experiment is repeated, applying ultrasonic energy at 25 MHz during the flow through period.

During the course of treatment, calcium and phosphate concentration released from the test valves are measured, and rates of demineralization are determined. The valves are evaluated for the extent of remaining biomineralization and the extent of tissue damage (if any) after each experimental protocol. Physiological function tests are also performed following the contact with the acidic treatment solution.

The following parameters are evaluated and optimized alone or in combination: pH, and sonic power. The carbonated apatite of biomineralized heart valve tissue is more soluble under acidic conditions. The pH ranges to be evaluated are below about 7.0, typically below about 4.0, and optimally about 1.0. Sonic power accelerates reactions in solution. Sound frequencies in the range of 20 kHz to 100 kHz are evaluated, typically about 25 kHz.

Example 2

Human Aortic Valve Tests in a Porcine Model

The most common causes of pure aortic stenosis are calcification of bicuspid valves, commissural fusion, degenerative calcification of tricuspid valves, cuspid fibrosis, and postinflammatory calcification of rheumatic origin. Calcified valves removed from human patients are transplanted into pigs. The animals are allowed to recover, and are then subjected to demineralization therapy with the acidic treatment solution. Devices for applying the acidic treatment solution to the stenotic aortic valves are made to either apply to a beating heart or a stopped heart. Devices applied to the beating heart will introduce the acidic treatment solution at a specific temperature and pH in conjunction with sonic power. For example, the acidic treatment solution is introduced across the base of the valve leaflets through a half doughnut shaped device as depicted in FIG. 3, semicircular in cross section on either side of the valve. Devices applied to the stopped heart, or to a bypassed heart which is still beating, will isolate the aortic valve region form the blood stream and circulate and cycle demineralizing solution through the aortic valve region.

The surgeon attempts to create grain boundary separations between individual grains of the carbonated apatite (dahllite), which composes the calcified tissue. Acidic solutions preferentially dissolve the calcium phosphate mineral at grain boundaries. Combined with ultrasonic power, this serves to loosen individual grains without having to dissolve the entire grain. Loose grains are removed with the circulating solution. Organic matrices entombed within the mineralized deposit may shield the mineral phase from the acidic treatment solution, necessitating solutions that are efficient in removing elements of an organic matrix from the grain boundary regions. Thus, one can supplement the acidic treatment solution with proteases, surfactants, detergents, oxidants and the like, at concentration sufficient to remove organic matrix without undue damage to the tissue under treatment. Alternatively, the supplements can be provided in one or more individual solutions and alternated with the acidic treatment solution. The removal of the organic matrix exposes the mineral to subsequent treatment with acidic treatment solution. Various solutions can be suction-pumped through the treated region through tubing. In this embodiment, both in-current and out-current flows are present. The out-current flow carries the cycled solutions, the dissolved ions from the mineral with organic debris, and loose pieces of mineralized deposits which become dislodged from the attached mineralized mass before dissolution of the mineral deposit is complete. Different solutions are cycled through the test region from a single site outside the body. Progression of demineralization is monitored using standard echocardiographic methods.

Following the above protocol, the animals are sacrificed and the heart valves are subjected to histological examination and further assays for mineral content.

Example 3

Formulation

| A) A suitable formulation for acidic treatment under a constant flow rate comprises: | |
|---|---|
| Formic acid (concentrated) | 10% |
| Sodium dodecyl sulfate (SDS) | 0.1% |
| $H_2O$ qs | 100% |
| B) An alternative formulation for acidic treatment under a constant flow rate comprises: | |
| HCl (concentrated) | 10% |
| EDTA | 0.1% |
| $H_2O$ qs | 100% |
| C) An alternative formulation for acidic treatment under a constant flow rate comprises: | |
| Phosphoric acid (concentrated) | 10% |
| $H_2O$ qs | 100% |
| D) An alternative formulation for acidic treatment under a constant flow rate comprises: | |
| Sulfuric acid (concentrated) | 10% |
| $H_2O$ qs | 100% |
| E) An alternative formulation for acidic treatment under a slower rate or under static conditions comprises: | |
| Tris HCl | 0.1 M |
| pH adjusted to 42 with concentrated HCl. | |

Example 4

The Sheep Model

To evaluate the efficacy of an acidic treatment solution in vivo, a sheep model is utilized. In this model, porcine aortic valved conduits are treated with 0.625% glutaraldehyde in vitro, and transplanted into the descending thoracic aorta in juvenile sheep (see Chanda, J., et al., 1997, Biomaterials 18:1317–1321, herein incorporated by reference). The calcification of the transplanted porcine valves are then analyzed by gross inspection, radiography, light, transmission, and surface scanning electron microscopy, or calcium analysis by absorption spectroscopy can be performed (see Schoen, F. J., et al., 1994, J. Thorac. Cardiovasc. Surg. 108:880–887). Any tissue damaged is also assessed by light microscopy. The protocols of Example 2 are then repeated.

Example 5

Analysis of Aortic Valve Mineralization

Two human aortic heart valves were removed during routine valve replacement therapy. These valves were dissected to separate mineralized deposits on the valve leaflets. The deposits where strongly adherent to the valve tissue and were incorporated into the structure of the leaflets as nodules. Both valves had extensive mineralize nodule formation. The nodules were hard and could not be fractured by hand. Contact x-rays were taken to document the extent and distribution of the mineralized nodules in the valve tissue. The mineralized areas demonstrated a radioopacy similar to well mineralized bone.

Figure 4A:
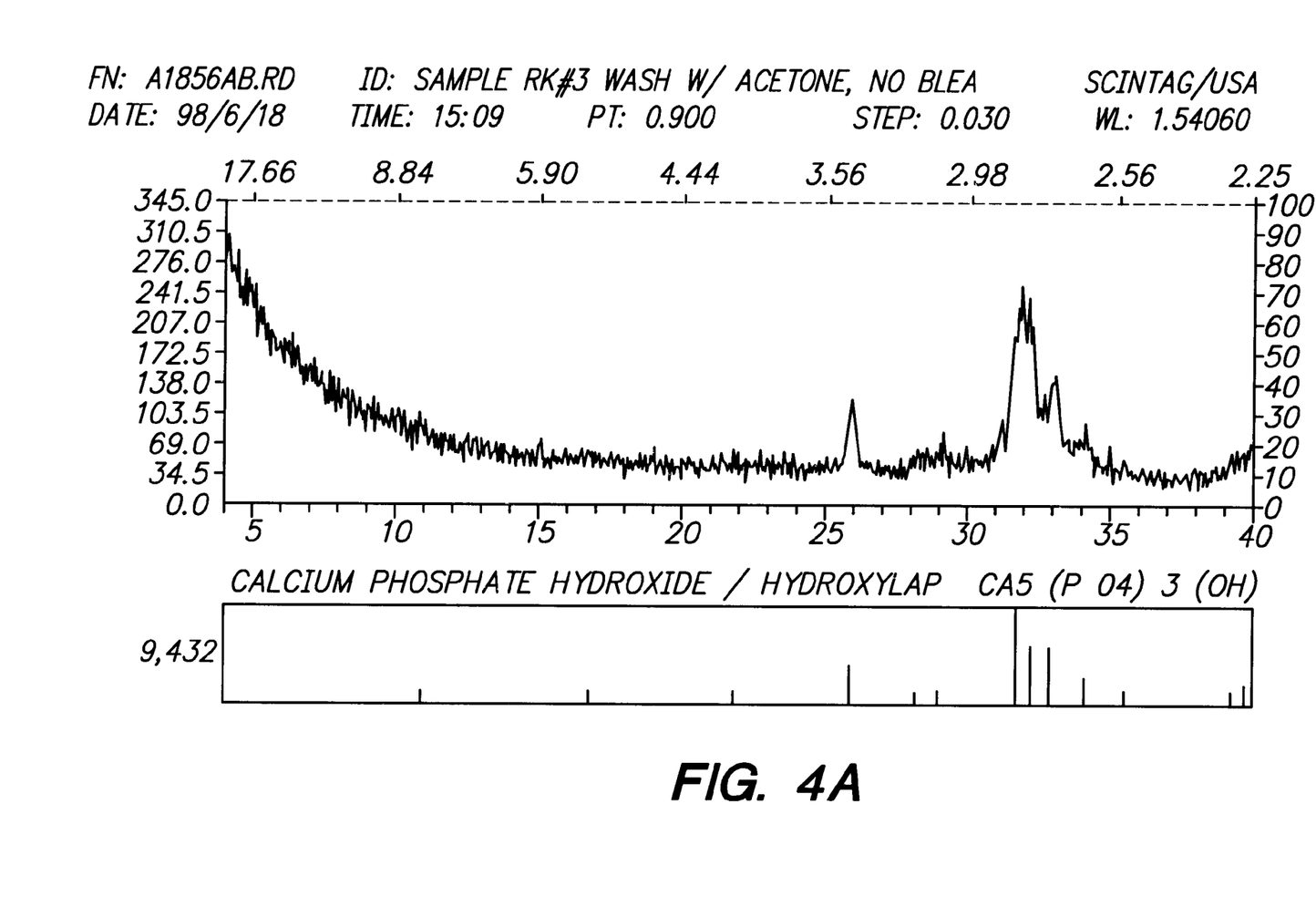
FIG. 4A is an x-ray diffraction pattern (XRD) of an intact mineralized lesion directly isolated from an excised human aortic heart valve leaflet.
Figure 4B:
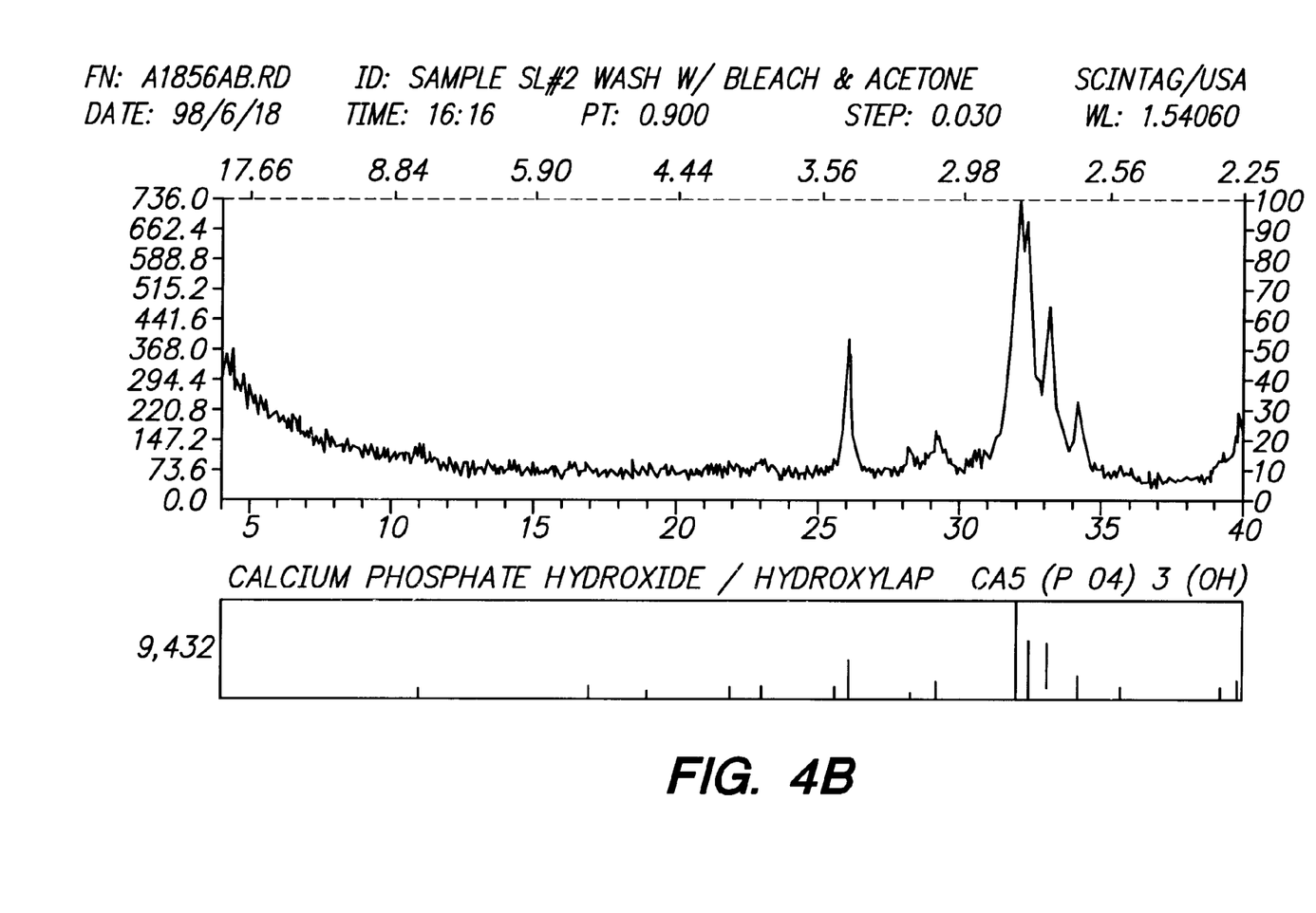
FIG. 4B is a x-ray diffraction pattern of a mineralized lesion following treatment with sodium hypochlorite
Figure 5A:
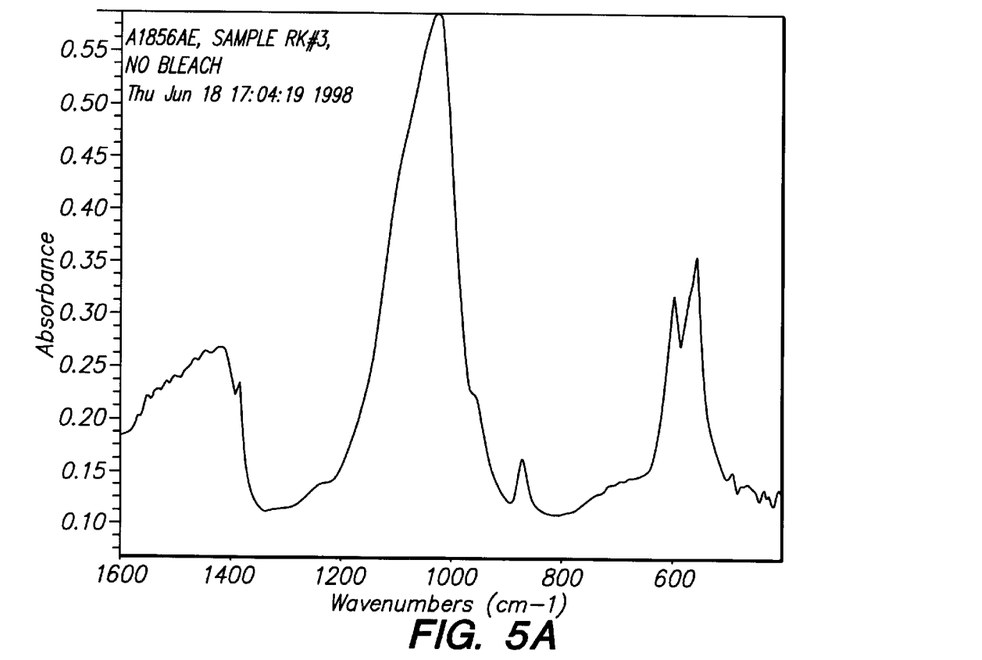
FIG. 5A is a Fourier transform infra-red (FTIR) spectrogram of an intact mineralized lesion directly isolated from an excised human aortic heart valve leaflet.
Figure 5B:
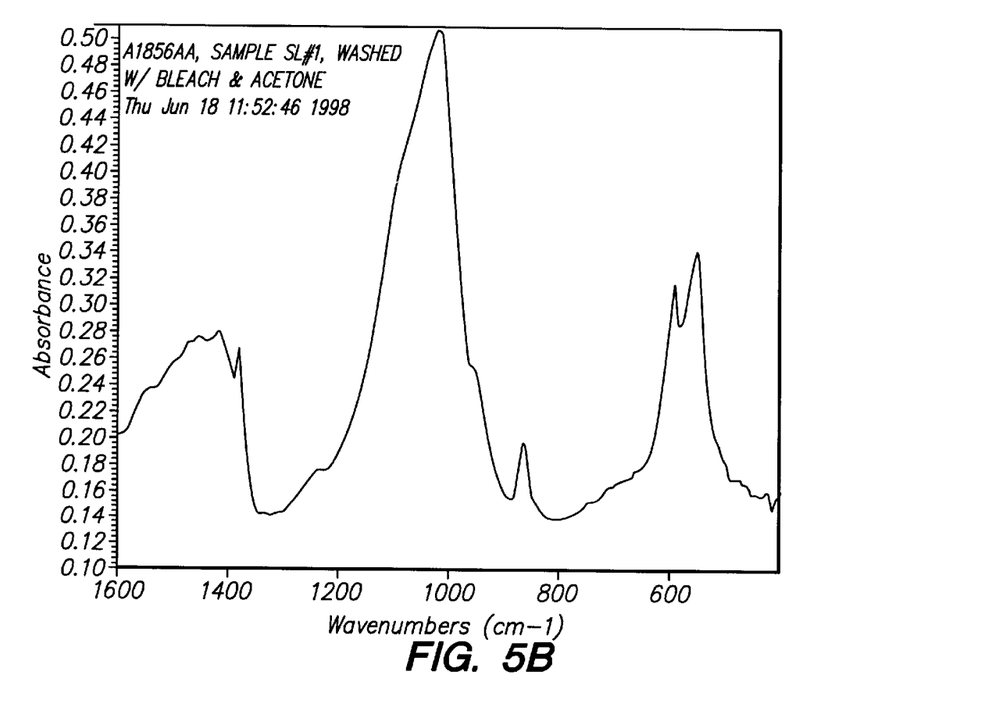
FIG. 5B is a FTIR of a mineralized lesion following treatment with sodium hypochlorite.

X-ray diffraction (XRD, see FIGS. 4A and 4B) and Fourier Transform Infra Red Spectroscopy (FTIR, see FIGS. 5A and 5B) were performed using standard procedures (see Constantz, B. R., et al. 1995, Science 267: 1796–1799, herein incorporated by reference) on the removed samples both directly (see FIGS. 4A and 5A) and following removal of most organic material with sodium hypochlorite (CLOROX bleach, see FIGS. 4B and 5B). The XRD pattern of the mineralized tissue, both with and without the organics removed, showed the characteristic peaks of apatite. The reflections were poorly crystalline in nature, indicating small crystal size and low levels of crystalline order. The FTIR spectrogram of the mineralized tissue, both with and without the organics removed, further identify the mineralized deposit as apatite that contains substantial carbonate, termed a carbonated apatite (mineral name, dahllite).

Samples were prepared for scanning electron microscopy, using the methods of Constantz, B. R., 1986 (In: *Reef Diagenesis*, Schroeder, J., and Puser, B., (eds.), Springer-Verlag). The size of the crystals composing the mineralized deposit were less than one micron across. The solubility of the crystals in this size range is expected to modify by an order of magnitude due to their increased surface are to volume ratio (see Constantz, B. R., et al., 1986, supra).

The composition of the "calcific deposits" are not hydroxyapatite as commonly published, rather they are a carbonated apatite, dahllite, which is expected to be considerably more soluble than hydroxyapatite. Also the size and crystallinity of the crystals of dahllite comprising these deposits are that of very small, high surface are to volume ratio crystallites whose diffraction patterns indicate a very low degree of crystalline order, further increasing their solubility.

Example 6

Cadaver Study

Human coronary arteries are harvested from heart transplants. Contact x-rays are taken to document the extent and distribution of the mineralized lesions in the harvested arteries. The arteries are ligated at either end to 5 mm polypropylene tubing and a pumping means is employed to produce a flow through device. A carbonic acid solution having a pH of 2.5 to 3.0 is flowed through the artery for a period of 20 minutes. During this period, intravascular ultrasound (IVUS) is employed to monitor the lesion in real time. The carbonic acid solution that has passed through the artery is collected and analyzed for dissolved calcium content using standard analytical methods. A graph is plotted of the mineral content of the collected solution vs. time. Following treatment, a second contact X-ray is taken to assess the extent of the mineralized lesion remaining in the artery. Finally, an ash weight test is performed of the remaining mineral. It is observed in the above assays that flowing a carbonic acid solution through the coronary artery reduces the mineral content of the lesion in the artery. Additional arteries are assayed according to the above methods, with the difference being that flow through times of 30, 60, 90 and 120 minutes are employed.

Example 7

Rabbit Study

To compare the effect of using a carbonic acid dissolution solution according to the subject invention with the effect of mechanical debridement as produced by a balloon catheter on arterial tissue, the following experiments are performed. Three groups of New Zealand white rabbits are formed, 5 rabbits per group. In each group, the right femoral and iliac arteries are treated with a first treatment method (either dissolution fluid or mechanic debridement) and the left iliac or femoral arteries are treated with another method or left untreated to serve as a control. The following table summarizes the treatment protocols.

| Group | Right Arteries | Left Arteries |
| --- | --- | --- |
| 1 | solution | (−) control |
| 2 | solution | (+) mechanical debridement |
| 3 | (+) mechanical debridement | (−) control |

Following 1, 7, 30 & 90 days, the animals are sacrificed and the illiac and femoral arteries harvested for analysis. The arteries are histographically analyzed for evidence of mechanical insult response and the presence of smooth epithelial cells. It is expected that the solution treated arteries appear similar to the control arteries, while the arteries subject to mechanical debridement show a mechanical insult response.

Example 8

Mineral Study

Norian SRS® cement (obtained from Norian Corporation, Cupertino, Calif.) is prepared according to the manufacturer's instructions. The resultant paste is placed into Teflon mold rings and allowed to set to produce dahllite disks. The disks are then contacted with the following solutions: 0.1 M HCl, 1.0 M HCl, concentrated HCl, 0.1 M HCl+0.01 M EDTA, 1.0 M HCl+0.01 M EDTA, concentrated HCl+0.1 M EDTA, 0.1 M $H_2SO_4$, 1.0 M $H_2SO_4$, 0.1 M $H_2SO_4$+0.01 M EDTA, 1.0 M $H_2SO_4$+0.1 M EDTA, 1.0 M formic acid, concentrated fromic acid, 1.0 M formic acid+0.1 M EDTA, 1.0 M acetic acid, concentrated acetic acid, 1.0 M acetic acid and 0.1 M EDTA, 1.0 M succinic acid, 1.0 M succinic acid+0.1 M EDTA; 0.1 M carbonic acid; and 1.0 M carbonic acid. A dissolution graph is then prepared for each solution which plots $Ca^{2+}$ concentration over time. By comparing the different dissolution graphs, the solubility of dahllite in different dissolution solutions is compared.

It is evident from the above results and discussion that improved methods of treating a host suffering from a vascular disease characterized by the presence of a calcified lesion are provided. The subject methods can be performed in a minimally invasive manner, thereby providing all of the advantages attendant therewith, such as reduced trauma to the patient and faster healing times. As the subject methods do not mechanically damage the vascular tissue of the patient, complications such a restinosis are avoided. Furthermore, the subject methods provide an effective and efficient means for removing calcified lesions from vascular tissue.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A catheter comprising:
   a dissolution fluid introduction lumen comprising an acidic dissolution fluid having a pH of less than about 2, wherein introduction lumen is capable of delivering a dissolution fluid to a vascular tissue site and
   a fluid removal lumen capable of removing fluid from said vascular tissue site having dimensions sufficient to allow passage of lesion debris.

2. The catheter according to claim 1, wherein said catheter further comprises a means for substantially isolating said vascular tissue site.

3. The catheter according to claim 2, wherein said means for substantially isolating said vascular tissue site is a double balloon system.

4. A system for flushing a vascular tissue site with a dissolution fluid, said system comprising:
   (a) a catheter comprising a dissolution fluid introduction lumen capable of delivering fluid to said vascular tissue site and a fluid removal lumen capable of removing fluid and lesion debris from said vascular tissue site;
   (b) a first pumping means operatively linked to said fluid introduction lumen in a manner sufficient such that said first pumping means forces fluid out of the distal end of said fluid introduction lumen;
   (c) a second pumping means operatively linked to said fluid removal lumen in a manner sufficient such that said second pumping means sucks fluid into the distal end of said fluid removal lumen; and
   (d) a dissolution fluid having a pH of less than about 2.

5. A kit for at least reducing the mineral content of a vascular calcified lesion, said kit comprising:
   a fluid capable of locally increasing the proton concentration in the region of said calcified lesion, said fluid having a pH of less than about 2; and
   a catheter fluid introduction means.

6. The kit according to claim 5, wherein said kit further comprises instructions for practicing a method of reducing or eliminating the mineral content of a vascular calcified lesion using a solution having a pH of less than about 2.

* * * * *